United States Patent
Schmitz et al.

(10) Patent No.: US 10,533,976 B2
(45) Date of Patent: Jan. 14, 2020

(54) ULTRASONIC INSPECTION SYSTEM

(71) Applicant: General Electric Company, Schenectady, NY (US)

(72) Inventors: Stephan Schmitz, Cologne (DE); Stephan Falter, Simmerath (DE); Wolfgang Dick, Kreuzau (DE); Thomas Weise, Weilerswist (DE); Matthias Schwabe, Cologne (DE)

(73) Assignee: General Electric Company, Schenectady, NY (US)

( * ) Notice: Subject to any disclaimer, the term of this patent is extended or adjusted under 35 U.S.C. 154(b) by 224 days.

(21) Appl. No.: 15/464,946

(22) Filed: Mar. 21, 2017

(65) Prior Publication Data
US 2017/0276649 A1   Sep. 28, 2017

Related U.S. Application Data

(60) Provisional application No. 62/313,251, filed on Mar. 25, 2016.

(51) Int. Cl.
*G01N 29/04* (2006.01)
*G01N 29/28* (2006.01)
*G01N 29/27* (2006.01)

(52) U.S. Cl.
CPC .......... *G01N 29/27* (2013.01); *G01N 29/043* (2013.01); *G01N 29/28* (2013.01);
(Continued)

(58) Field of Classification Search
CPC ...... G01N 29/043; G01N 29/27; G01N 29/28; G01N 29/221; G01N 29/223; G01N 29/26;
(Continued)

(56) References Cited

U.S. PATENT DOCUMENTS 3,285,059 A    11/1966  Bogle
3,508,436 A *   4/1970  Krautkramer ........ G01N 29/265
                                                    73/637
(Continued)

FOREIGN PATENT DOCUMENTS

DE    28 06 550 A1    8/1979
GB    2 027 199 A     2/1980

OTHER PUBLICATIONS

Extended European Search Report and Opinion issued in connection with corresponding EP Application No. 17162638.5 dated Jun. 30, 2017.

*Primary Examiner* — Jacques M Saint Surin
(74) *Attorney, Agent, or Firm* — Mintz Levin Cohn Ferris Glovsky and Popeo, P.C.

(57) ABSTRACT

An ultrasonic matrix phased array inspection system can include a plurality of curved matrix phased array probes surrounding a test chamber through which a longitudinal test object passes. Fluid injectors can provide a rotating fluid jacket around the longitudinal test object to ultrasonically couple the plurality of curved matrix phased array probes to the longitudinal test object. The plurality of curved matrix phased array probes can remain in a fixed position during inspection and can inspect the longitudinal test object by transmitting ultrasonic sound waves at various angles to identify flaws of any orientation.

19 Claims, 8 Drawing Sheets

(52) U.S. Cl.
CPC ............... *G01N 2291/0289* (2013.01); *G01N 2291/106* (2013.01); *G01N 2291/262* (2013.01)

(58) Field of Classification Search
CPC ......... G01N 29/262; G01N 2291/0289; G01N 2291/106; G01N 2291/2634; G01N 2291/2626; G01N 2291/262
USPC .......................................................... 73/640
See application file for complete search history.

(56) References Cited

U.S. PATENT DOCUMENTS

| | | | | |
|---|---|---|---|---|
| 3,600,613 | A | * | 8/1971 | Clarke ................. G01N 29/265 310/336 |
| 5,569,865 | A | * | 10/1996 | Profe ..................... B65H 51/16 28/248 |
| 6,215,836 | B1 | * | 4/2001 | Walker ................... B23K 31/12 324/220 |
| 6,739,188 | B1 | | 5/2004 | Prause |
| 7,429,352 | B2 | | 9/2008 | Bisiaux et al. |
| 2008/0054091 | A1 | * | 3/2008 | Babaev ..................... B01F 3/08 239/102.2 |
| 2008/0236286 | A1 | | 10/2008 | Lam et al. |
| 2012/0310551 | A1 | * | 12/2012 | Na ..................... G01N 29/0645 702/39 |
| 2014/0165730 | A1 | * | 6/2014 | Na ..................... G01N 29/0645 73/588 |
| 2015/0253288 | A1 | * | 9/2015 | Spencer ................. G01N 29/24 73/602 |
| 2016/0231291 | A1 | * | 8/2016 | Boulware ............ G01N 29/262 |

\* cited by examiner

ULTRASONIC INSPECTION SYSTEM

CROSS-REFERENCE TO RELATED APPLICATIONS

This application claims the benefit of and priority to U.S. Provisional Patent Application Ser. No. 62/313,251, filed Mar. 25, 2016, and entitled "ULTRASONIC MATRIX PHASED ARRAY INSPECTION SYSTEM," the entirety of which is incorporated herein by reference.

BACKGROUND

The subject matter disclosed herein relates to ultrasonic inspection systems, and more specifically, an ultrasonic matrix phased array inspection system.

Nondestructive testing devices can be used to inspect test objects to detect and analyze anomalies in the objects. In an ultrasonic inspection system, electrical pulses are transmitted to an ultrasonic probe where they are transformed into ultrasonic pulses by one or more ultrasonic transducers (e.g., piezoelectric elements) in the ultrasonic probe. During operation, the electrical pulses are applied to the electrodes of one or more ultrasonic transducers, generating ultrasonic waves that are transmitted into the test object to which the probe is coupled. In some ultrasonic inspection systems, ultrasonic waves are transmitted directly from the ultrasonic probe into the test object, while in other ultrasonic inspection systems, the ultrasonic waves are transmitted from the ultrasonic probe to the test object indirectly through a fluid (e.g., water) between the probe and the test object. As the ultrasonic waves pass through the test object, various reflections, called echoes, occur as the ultrasonic wave interacts with anomalies in the test object. Conversely, when an ultrasonic wave is reflected back from the test object and is received by the piezoelectric surface of the ultrasonic transducers, it causes the transducers to vibrate generating a voltage difference across the electrodes that is detected as an electrical signal received by signal processing electronics. By tracking the time difference between the transmission of the electrical pulse and the receipt of the electrical signal, and measuring the amplitude of the received electrical signal, various characteristics of the anomaly (e.g., depth, size, orientation) can be determined.

Ultrasonic inspection systems may be used to inspect longitudinal test objects having an elongated longitudinal axis, such as bar stock or tubes, for various flaws or defects in manufacturing, including longitudinal defects, transverse defects, and oblique defects. In order to inspect the longitudinal test objects for defects existing at different orientations, ultrasonic inspection systems may employ a plurality of ultrasonic probes surrounding the longitudinal test object and then rotate and maneuver the ultrasonic probes around the longitudinal test object as the test object is transported through the ultrasonic inspection system. The requirement that the ultrasonic probes rotate and maneuver about the longitudinal test object results in a mechanically complex ultrasonic inspection system that is expensive to manufacture and can require a significant amount of maintenance.

BRIEF DESCRIPTION OF THE INVENTION

An ultrasonic matrix phased array inspection system is disclosed. The inspection system can include a plurality of curved matrix phased array probes surrounding a test chamber through which a longitudinal test object passes. Fluid injectors can provide a rotating fluid jacket around the longitudinal test object to couple the plurality of curved matrix phased array probes to the longitudinal test object. The plurality of curved matrix phased array probes can remain in a fixed position during inspection and can inspect the longitudinal test object by transmitting ultrasonic sound waves at various angles to identify flaws of any orientation. An advantage that may be realized in the practice of some disclosed embodiments of the ultrasonic matrix phased array inspection system is that the system can identify flaws of any orientation without having to rotate or otherwise maneuver the plurality of curved matrix phased array probes or rotate the longitudinal test object.

In one embodiment, an ultrasonic inspection system is described. The ultrasonic inspection system includes a test chamber configured to receive a test object. The test chamber includes a plurality of ultrasonic probes aligned coaxially along an axis, each ultrasonic probe including a phased array of ultrasonic transducers. The test chamber additionally includes a plurality of fluid injectors interspersed with the plurality of ultrasonic probes coaxially along the axis and configured to generate a rotating fluid jacket around the test object. A fluid supply system is coupled to the plurality of fluid injectors to supply fluid to the plurality of fluid injectors. The plurality of ultrasonic probes is configured to generate ultrasonic waves in a rotating sound field around a circumference of the test object to identify an anomaly in the test object.

In another embodiment, an ultrasonic inspection system is described. The ultrasonic inspection system includes a plurality of ultrasonic probes. Each ultrasonic probe includes a phased array of ultrasonic transducers. The plurality of ultrasonic probes is aligned along an axis to define a test chamber. The plurality of ultrasonic probes is configured to transmit ultrasonic waves to a test object in the test chamber to identify anomalies in the test object with the plurality of ultrasonic probes configured to remain in a fixed position during inspection of the test object.

In yet another embodiment, a method for inspecting a test object with an ultrasonic inspection system is described. The ultrasonic inspection system includes a test chamber defined by a plurality of phased array ultrasonic probes aligned along an axis. Each probe has a curved inner surface and an array of ultrasonic transducers. A plurality of fluid injectors is interspersed among the plurality of phased array probes along the axis. Each fluid injector includes a curved interior surface, the interior surfaces of the ultrasonic probes and of the fluid injectors defining a test chamber.

The method includes advancing a test object through the test chamber. Ultrasonic waves are transmitted, via the ultrasonic transducers of the plurality of ultrasonic probes, in a rotating sound field around a circumference of the test object as the test object advances through the test chamber. Ultrasonic waves reflected from the test object are received at the ultrasonic transducers.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the disclosed subject matter encompasses other embodiments as well. The drawings are not necessarily to scale, emphasis generally being placed upon illustrating the features of certain embodiments of the invention. In the drawings, like numerals are used to indicate like parts throughout the various views.

DETAILED DESCRIPTION

Embodiments of the disclosed subject matter provide an ultrasonic matrix phased array inspection system. The inspection system can include a plurality of curved matrix phased array probes surrounding a test chamber through which a longitudinal test object passes. Fluid injectors can provide a rotating fluid jacket around the longitudinal test object to couple the plurality of curved matrix phased array probes to the longitudinal test object. The plurality of curved matrix phased array probes can remain in a fixed position during inspection and can inspect the longitudinal test object by transmitting ultrasonic sound waves at various angles to identify flaws of any orientation. Other embodiments are within the scope of the disclosed subject matter.

Figure 1:
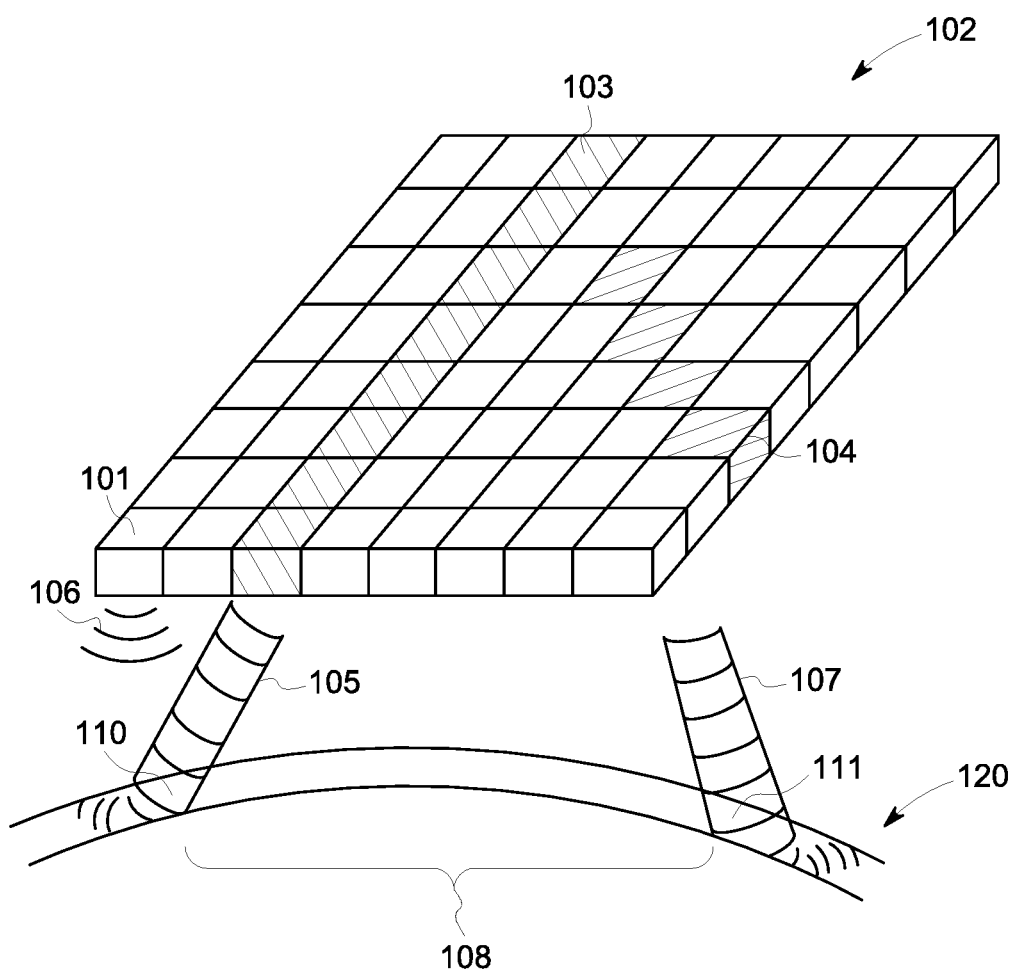
FIG. 1 is a schematic diagram of an embodiment of an ultrasonic matrix phased array scanning a test object.
Figure 2:
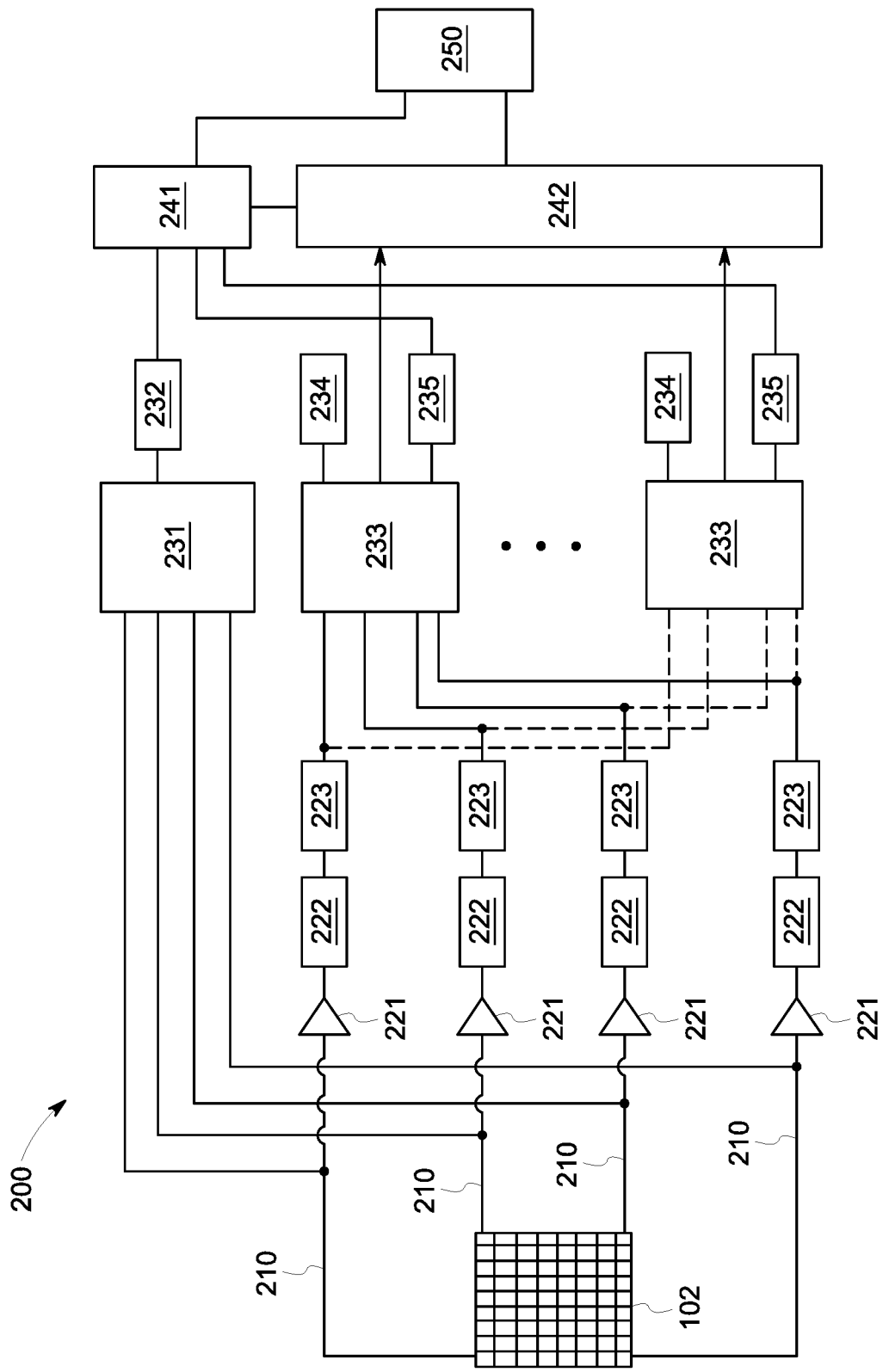
FIG. 2 is a diagram of an embodiment of a signal processing system for controlling an ultrasonic matrix phased array.

FIG. 1 is a schematic diagram of an embodiment of a two dimensional ultrasonic matrix phased array 102 whose transmitted ultrasonic waves 105, 107 are directed at a test object 120. FIG. 2 is a diagram of an embodiment of a signal processing system 200 for controlling the ultrasonic matrix phased array 102 of FIG. 1. Typically, the ultrasonic matrix phased array 102 is disposed within a probe (not shown) as part of an ultrasonic inspection system, but is shown in FIG. 1 in schematic form. While illustrated in FIG. 1 as an 8×8 array, the illustrated arrangement of transducers 101 in the ultrasonic matrix phased array 102 is not intended to limit possible configurations, as the number and arrangement of transducers 101 can assume various quantities and layouts.

Each transducer 101 can be capable of transmitting ultrasonic pulses 106 toward a test object 120 (e.g., through a water column) in a direction that is fixed according to the orientation of the transducer 101. A plurality of ultrasonic pulses 106 from a plurality of transducers 101 can produce an ultrasonic wave at a predetermined angle. Each transducer 101 can also receive ultrasonic waves reflected from the test object 120. The transmission and receipt of the ultrasonic waves can be controlled by a signal processing system 200, described below. By controlling the timing of the ultrasonic pulses 106 from selected subsets of transducers 101 in the ultrasonic matrix phased array 102, the transmitted pulses 106 can be coordinated into directed ultrasonic waves 105, 107 and steered in the desired direction.

In an embodiment, a first subset 103 of transducers 101 can be controlled by the signal processing system 200 to transmit ultrasonic pulses, or pulse trains, in a coordinated time delay relationship to transmit a first ultrasonic wave 105 directed toward the test object 120 at a first angle determined by a first set of transmit delays. Similarly, a second subset 104 of transducers 101, different from the first subset 103 of ultrasonic transducers 101, can be controlled by the signal processing system 200 (FIG. 2) to transmit ultrasonic pulses in a coordinated time delay relationship to transmit a second ultrasonic wave 107 directed toward the test object 120 at a second angle, different from the first angle, determined by a second set of transmit delays. Other subsets of transducers 101 in the ultrasonic matrix phased array 102, comprising any number and combination of transducers 101, can be similarly selected and coordinated to transmit ultrasonic waves at various ranges of predetermined angles (e.g., 0 to 360 degrees). The ranges of predetermined angles can include a setup for different ultrasonic waves targeting different paths in a test object. The controlled coordination of the set of transmit delays for each subset of transducers 101 can determine the angle at which the ultrasonic wave is transmitted and, therefore, the angle at which the ultrasonic wave impacts the test object 120. This process of temporal pulse shaping can also control characteristics of the ultrasonic wave front, for example, its focus. Thus, multiple subsets of transducers 101 in the ultrasonic matrix phased array 102 can be programmably selected, and each subset independently coordinated with different sets of transmit delays for targeting the test object 120 with multiple ultrasonic waves. Two or more subsequent delay sets can be utilized to detect anomalies at different depths within a piece of material using different delay values.

Referring again to FIG. 1, there is illustrated an embodiment of a test area 108 through the material of the test object 120 bounded by the ultrasonic waves 105, 107. Anomalies 110, 111, illustrated here as being located in the path of the ultrasonic waves 105, 107, respectively, generate reflected ultrasonic waves that are received by the ultrasonic matrix phased array 102 and can be analyzed by the signal processing system 200 (FIG. 2). The location and orientation of an anomaly 110, 111 in the test object 120 can be detected using one or more of the ultrasonic waves transmitted at different angles. By correlating transmitted ultrasonic waves with received reflected ultrasonic waves, a location and orientation of an anomaly can be determined. Thus, the capability of transmitting ultrasonic waves at multiple angles from an ultrasonic matrix phased array 102 can produce an efficient ultrasonic inspection system configuration and methodology.

Generally, an anomaly 110, 111 can be indicated when the amplitude of a reflected ultrasonic wave deviates from an expected magnitude. A threshold deviation amount can be predetermined and programmed into the signal processing system 200 (FIG. 2), as explained below, to issue a notification signal when an anomaly 110, 111 is detected. The notification signal can include, for example, an audible signal or a stored flag for handling at a later time. The predesigned transmission patterns of ultrasonic pulses may include a series of transmit/receive scanning cycles which can rapidly test component areas for the presence of anomalies 110, 111 having various orientations in the test object 120.

With reference to FIG. 2, there is illustrated an embodiment of a signal processing system 200 connected to the ultrasonic matrix phased array 102 of FIG. 1 over control lines 210. While only four representative control lines 210 are shown in FIG. 2, each transducer 101 in the ultrasonic matrix phased array 102 is connected to the processing system 200 by a control line 210, with each control line 210 used for transmitting electrical signals to, and receiving electrical signals from, the ultrasonic matrix phased array 102. The modules of the signal processing system can include a variety of different devices, including field programmable gate arrays (FPGAs), application specific integrated circuits (ASICs), read only memory (ROM), random access memory (RAM), among others.

The signal processing system 200 can include a transmitter control module 231. Transmitter control module 231 can send electrical pulses to the transducers 101 in the ultrasonic matrix phased array 102 over control lines 210, which can convert the electrical pulses into ultrasonic pulses. A transmitter settings module 232 can provide the transmit delays for each of the transducers 101 to the transmitter control module 231 to coordinate a timing relationship for each subset of the transducers 101 to transmit an ultrasonic wave at a predetermined impact angle. The signal processing system 200 also can include a cycle control module 241 connected to the transmitter settings module 232 to coordinate and correlate the transmission of the transmitted ultrasonic waves at different impact angles. In addition to being connected to the transmitter control module 231, each transducer 101 of the ultrasonic matrix phased array 102 can be connected to an amplifier 221, filter 222, and A/D converter 223 for receiving and digitizing reflected ultrasonic waves from the test object 120 (FIG. 1). The reflected ultrasonic waves can be produced from the ultrasonic waves transmitted by the same ultrasonic matrix phased array 102.

The signal processing system 200 also can include a number of summer modules 233 connected to the A/D converters 223 for receiving digitized data representing the reflected ultrasonic waves from the test object. The summer modules 233 can be connected to A/D converters 223 to receive digitized outputs of the ultrasonic matrix phased array 102 in various combinations depending on the processing requirements for any particular testing scheme employed by the ultrasonic inspection system. Outputs from each of the summer modules 233 can be received for immediate processing at connected evaluation units 242, and/or they can be recorded in receiver storage modules 234, connected to each summer module 233, for processing at a later time. The summer modules 233 can receive inputs from the receiver settings module 235 that include delay data derived in combination with the coordinated transmit delays in the transmitter settings module 232, described above, under control of a cycle control module 241 for managing appropriate delay correlations between timed pulses for generating ultrasonic pulses and received reflected ultrasonic waves.

Evaluation units 242, connected to receive outputs from the summer modules 233 and connected to the cycle control module 241, can analyze the ultrasonic digitized data and generate A-scan information as an output to the processing electronics 250. Threshold deviation magnitudes for triggering anomaly determinations can be programmed into the evaluation units 242 so that the anomaly indications are included in the A-scan output. The evaluation units 242 can be configured to receive data from each of the summer modules 233 for immediate processing, and/or they can receive previously stored data from receiver storage modules 234. The processing electronics 250 can include a personal computer or digital signal processor (DSP) for managing the inputs/outputs of the signal processing system 200, which includes control and reception data to and from the ultrasonic matrix phased array 102, storage, a user interface, which can be used technicians, and may include selecting controls for how to handle or issue notifications for detected anomalies, and for managing the display of processed scanning data for the test object 120.

Figure 3:
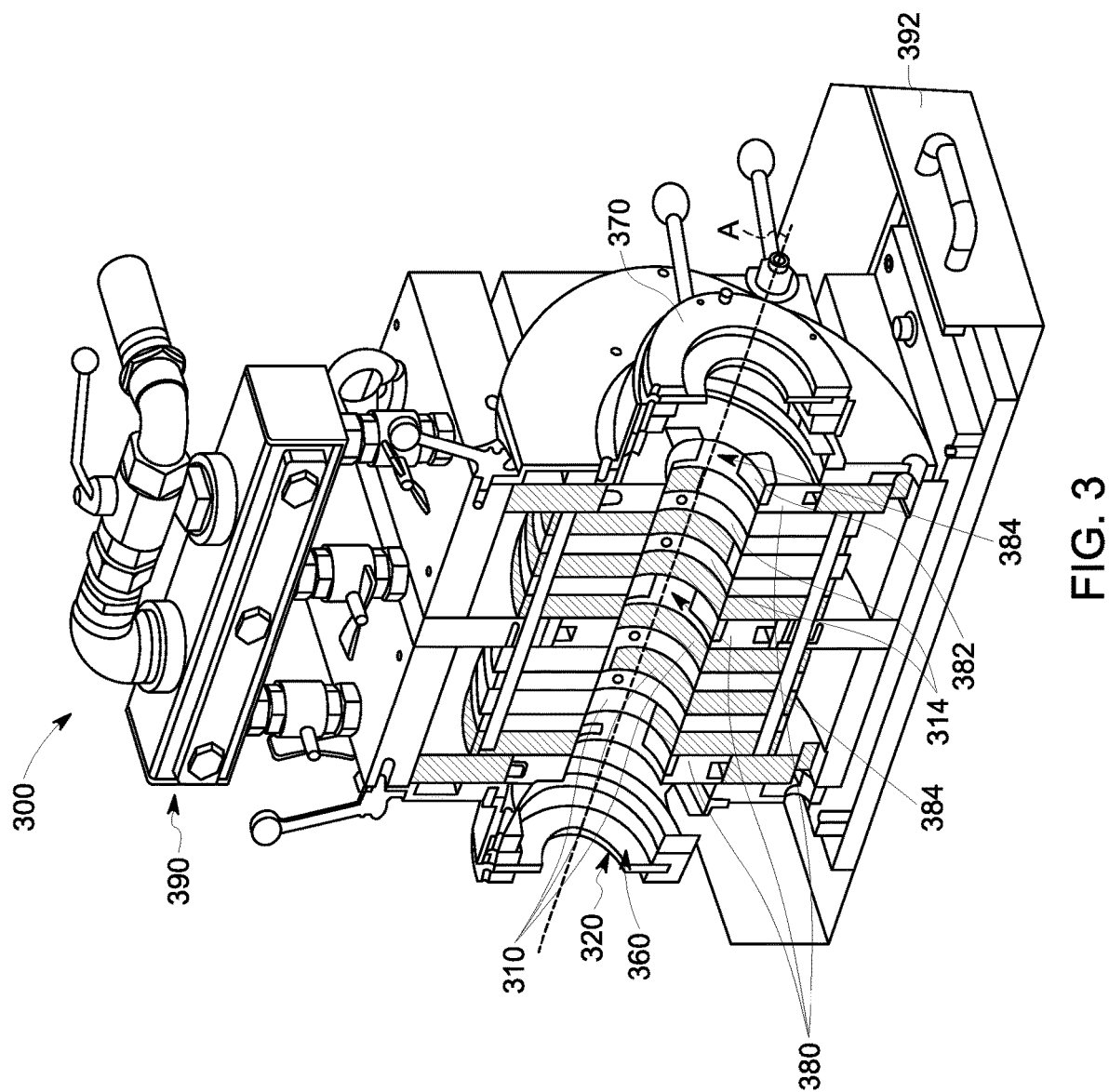
FIG. 3 is a partial sectional view of an embodiment of an ultrasonic matrix phased array inspection system.
Figure 4:
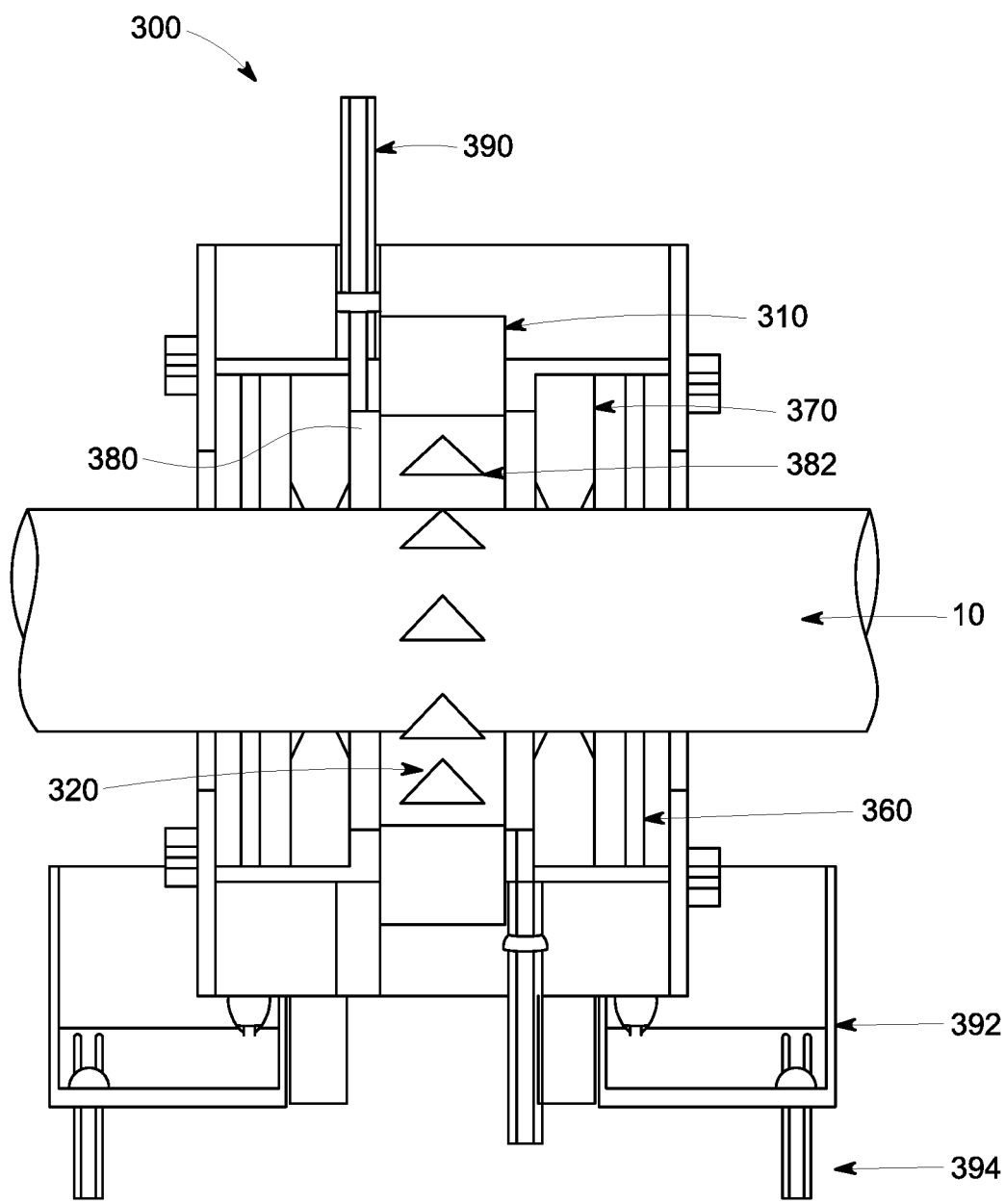
FIG. 4 is a cross-sectional view of the ultrasonic matrix phased array inspection system of FIG. 3.

FIG. 3 is a partial sectional view of an embodiment of a ultrasonic matrix phased array inspection system 300 and FIG. 4 is a cross-sectional view of the ultrasonic matrix phased array inspection system 300. The illustrated ultrasonic matrix phased array inspection system 300 can include a fluid supply system 390, a water collecting tray 392, a water outlet 394, fluid injectors 380, rubber seals 360, guide bushings 370, a test chamber 320, curved matrix phased array probes 310, and a computing device (not shown). In additional embodiments, the ultrasonic matrix phased array inspection system 300 may have supplementary components required for sealing the test chamber 320, such as rubber sealing, mounting the longitudinal test object 10 (shown in FIG. 4) (e.g., bar stock or a tube (round, square, hexagonal. etc.)), guiding the longitudinal test object 10, and/or electronic equipment for operating the ultrasonic matrix phased array inspection system 300 and processing the received data.

As illustrated, at least one of the phased array probes 310 can have a curved interior surface 314. In an embodiment, at least one of the phased array probes 310 can have an annular shape. Similarly, at least one of the fluid injectors 380 can have a curved interior surface 384. In an embodiment, at least one of the fluid injectors 380 can have an annular shape. As illustrated in FIG. 3, the plurality of phased array probes 310 can be aligned coaxially along an axis A. The fluid injectors 380 can be interspersed among the plurality of phased array probes 310 and can be aligned coaxially with the plurality of phased array probes 310. The interior surfaces 314 of the phased array probes 310 and the interior surfaces 384 of the fluid injectors 380 can define the test chamber 320, which extends along the axis A and defines a travel path for the test object.

The fluid supply system 390 can supply the fluid to the fluid injectors 380 and can provide sufficient force, such as centrifugal force, to produce a rotating fluid jacket 382 around the longitudinal test object 10. The fluid supplied by the fluid supply system 390 can be, but is not limited to water, oil, homogeneous fluids, or other types of fluids, fluid combinations, or fluids that are capable of propagating ultrasonic waves. The fluid supply system 390 can be connected to a pump (not shown) to power the flow of fluid through the fluid supply system 390. The fluid supply system 390 can be a closed system or an open system. The fluid supply system 390 can also connected to the computing device to provide the proper amount of fluid to the test chamber 320 for the type of immersion testing being performed.

Each of the fluid injectors 380 can have at least one nozzle 382 from which the fluid is discharged. In one embodiment, the fluid is discharged substantially tangentially to the interior surface 384 of the fluid injectors 380 and the test chamber 320 to produce the rotating fluid jacket 382. In additional embodiments, the fluid can be discharged at a variety of angles or directions provided the fluid produces a sufficient rotating fluid jacket 382 for the curved matrix phased array probes 310 to ultrasonically couple to the longitudinal test object 10. The fluid injectors 380 in FIG. 1 can have an interior surface 384 which can have a concave curvature to match or equal the curvature of the interior surface 314 of the curved matrix phased array probes 310 to form the test chamber 320.

Figure 5A:
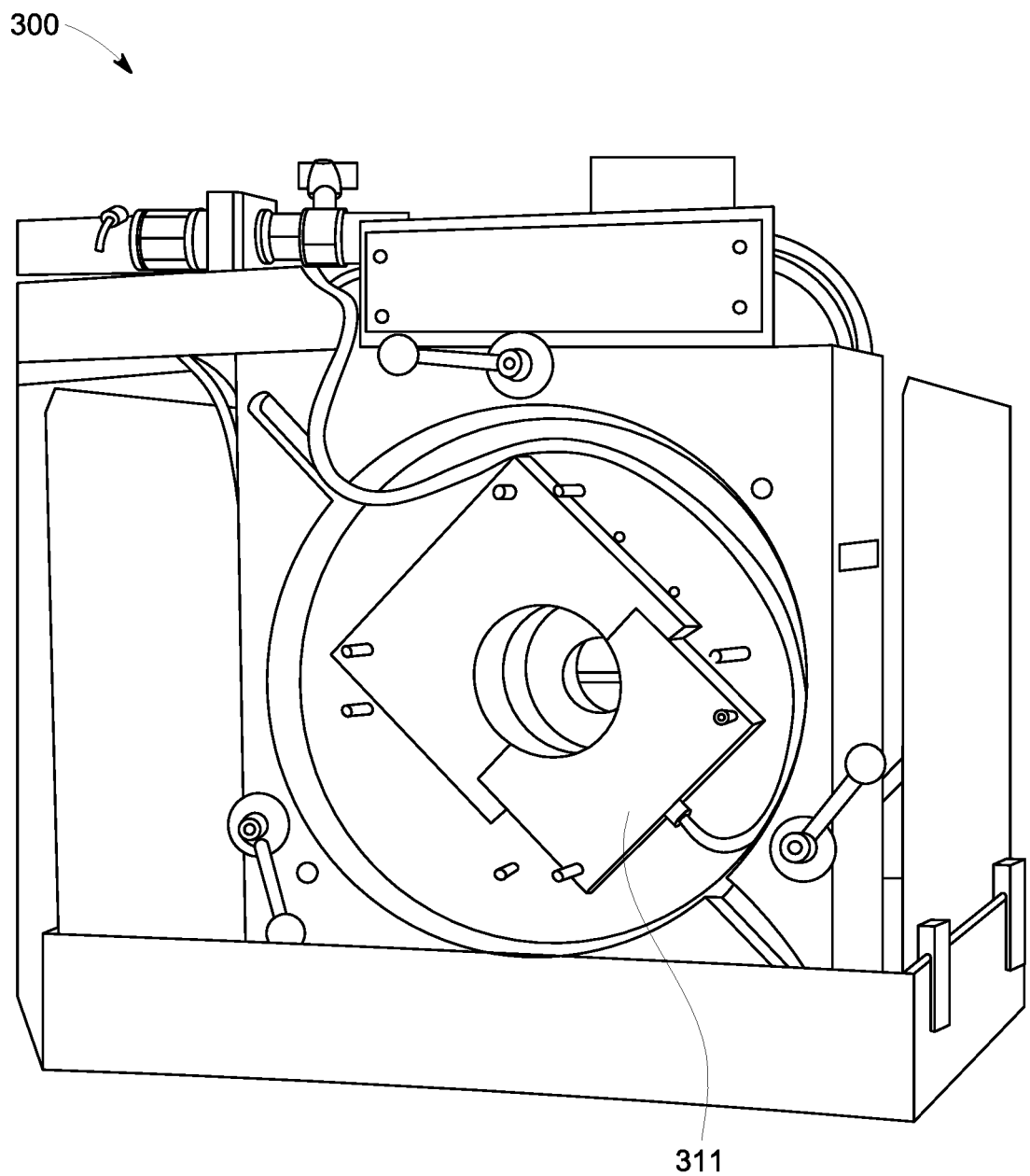
FIGS. 5A and 5B are illustrations of curved ultrasonic matrix phased array probes installed on an embodiment of ultrasonic matrix phased array inspection system.
Figure 5B:
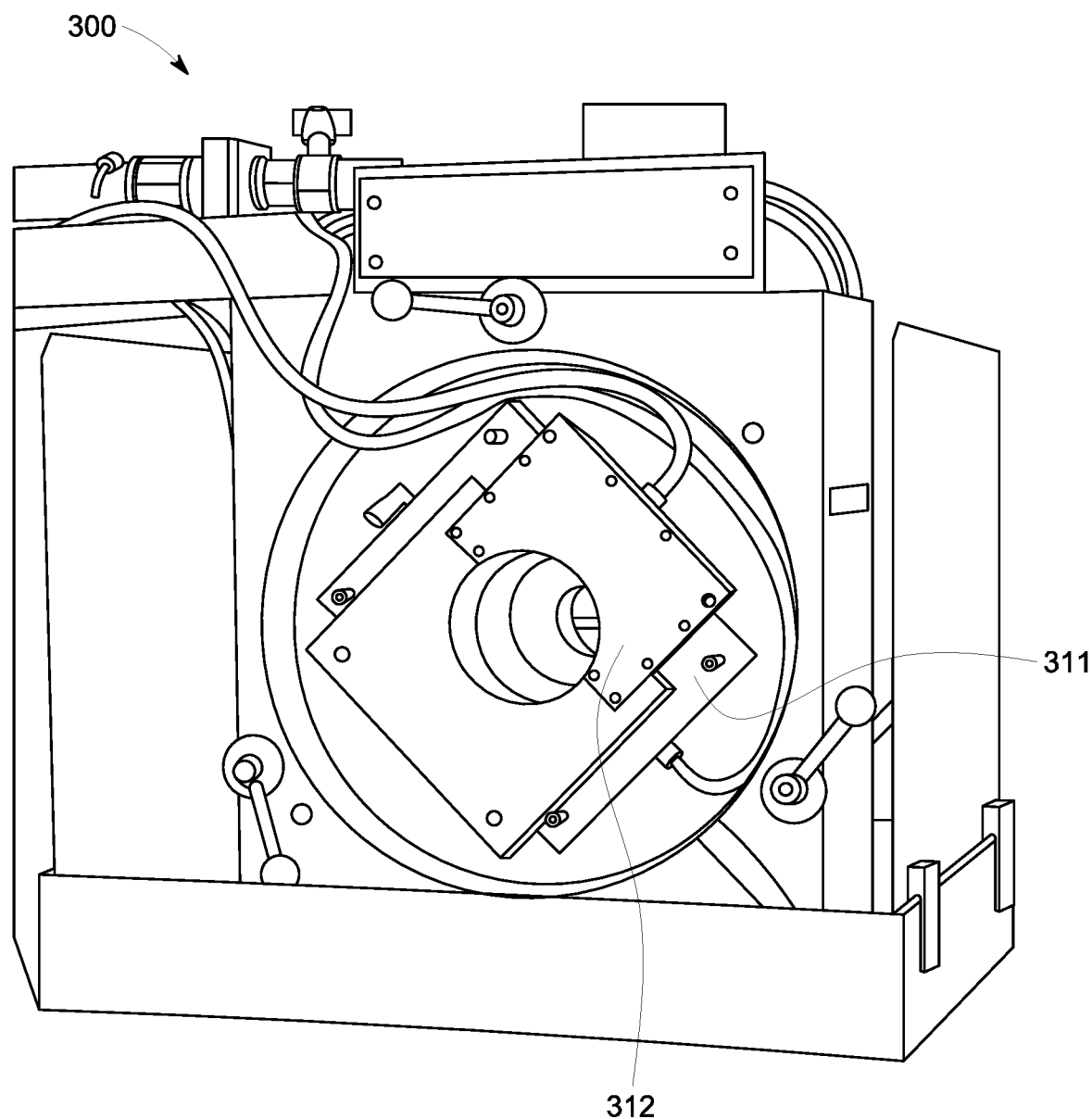

Each curved matrix phased array probe 310 can have a plurality of transducers (e.g., 32, 64, 128, or 256) placed on the interior surface 314 of the curved matrix phased array probe 310 directed at the longitudinal test object 10. In the embodiment shown in FIGS. 3 and 4, each curved matrix phased array probe 310 is located in a different plane and radially offset at a predetermined angle from the previous curved matrix phased array probe 310. As shown in FIGS. 5A and 5B, each of which illustrate an embodiment of a phased array inspection system, the first curved matrix phased array probe 311 can be radially offset from the second curved matrix phased array probe 312 at an angle of 90 degrees, requiring four curved matrix phased array probes to completely surround the longitudinal test object 10 and form the test chamber 320. Examples of possible offsets of transducers from one curved matrix phased array probe 310 to the next may be, but not limited to, zero (0) degrees to one hundred and eighty (180) degrees. Offsets between curved matrix phased array probe 310 transducers may be within the range of thirty (30) to one hundred and twenty (120) degrees. The offset can allow groups of transducers (e.g., 16 in a group) in the plurality of curved matrix phased array probes 310 to be activated sequentially to transmit ultrasonic waves in a rotating or oscillating sound field to the entire circumference of the longitudinal test object 10 as it passes linearly through the ultrasonic matrix phased array inspection system 300 without requiring any movement or rotation of the curved matrix phased array probes 310, which can remain in a fixed position. The ultrasonic waves produced by the transducers are, in some embodiments, configured to penetrate into longitudinal test object 10 and reflect off of areas or structures within the longitudinal test object 10, such as areas of decreased density, which may result from manufacturing imperfections, or other flaws within the longitudinal test object 10.

The fluid injectors 380 and the curved matrix phased array probes 310 can be attached or coupled to one another to form the testing chamber 320 of the ultrasonic matrix phased array inspection system 300. The fluid injectors 380 and the curved matrix phased array probes 310 can be connected to form a substantially fluid tight seal between one another. In the embodiment shown in FIG. 1 there are six (6) curved matrix phased array probes 310 placed between each of the fluid injectors 380. In additional embodiments, the number of curved matrix phased array probes 310 to fluid injectors 380 can be altered depending on the intended operation of the ultrasonic matrix phased array inspection system 300 (e.g., three probes up to twelve probes). The curved matrix phased array probes 310 can be arranged to overlap each other to provide sufficient coverage of the entire circumference of the longitudinal test object 10.

The interior surfaces 384 of the fluid injectors 380 can be flush with the interior surface 314 of the curved matrix phased array probes 310. By positioning the interior surface 384 of the fluid injectors 380 and the interior surface 314 of the curved matrix phased array probes 310 flush with one another, the fluid injectors 380 can produce the rotating fluid jacket 382 around the longitudinal test object 10 because the interior surfaces 314, 384 produce a smooth surface for the water to flow over. In additional embodiments, the interior surface 384 of the fluid injectors 380 and the interior surface 314 of the curved matrix phased array probes 310 can be positioned in numerous configurations, provided the fluid injectors 380 can produce a rotating fluid jacket 382 so the curved matrix phased array probes 310 can ultrasonically couple to the longitudinal test object 10.

A rubber seal 360 can be attached or coupled at both ends of the test chamber 320 to seal the test chamber 320. The rubber seal 360 can provide a substantially fluid tight seal around the longitudinal test object 10 to keep the fluid within the test chamber 320 and to keep foreign objects and fluids out of the test chamber 320. The longitudinal test object 10 may have other fluids or small debris, such as from the manufacturing or shipping process, contacting the exterior surface of the test object, which could cause errors or false detection of imperfections within the longitudinal test object 10. The rubber seal 360 can prevents such debris from entering the testing area. In additional embodiments, the fluid supply system 390 may be a closed system, and the rubber seals 360 keep the fluid used in the fluid supply system confined.

Guide bushings 370 can be used to guide the longitudinal test object 10 through the ultrasonic matrix phased array inspection system 300. In additional embodiments, the guide bushings 370 guide the longitudinal test object 10 through the ultrasonic matrix phased array inspection system 300. In some embodiments or applications, no guiding bushing is used (i.e., rubbers are used to shape the water jacket only)

Figure 6:
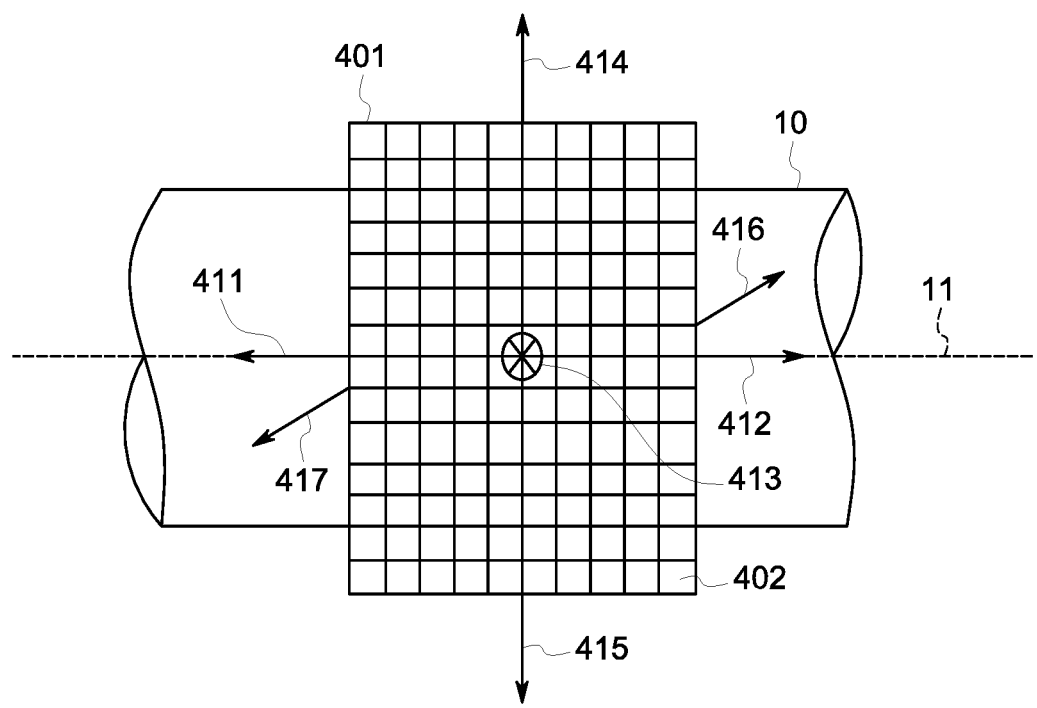
FIG. 6 is an illustrative diagram of an embodiment of a curved two-dimensional (2D) ultrasonic matrix phased array inspecting a longitudinal test object.

FIG. 6 is an illustrative diagram of an embodiment of a curved ultrasonic matrix phased array 402 inspecting a longitudinal test object 10 having a longitudinal axis 11. For illustrative purposes, FIG. 6 only shows the curved ultrasonic matrix phased array 402 for one of the plurality of curved ultrasonic matrix phased array probes 310 (FIG. 3) that would surround the test chamber 320 (FIG. 3). The embodiment of a curved ultrasonic matrix phased array 402 can include a plurality of transducers 401 arranged in a two-dimensional array (2D) with a symmetrical density vertically and horizontally. As discussed above, by activating certain groups of transducers 401, the curved ultrasonic matrix phased array 402 can transmit ultrasonic sound waves at various angles to identify flaws of any orientation. For example, the curved ultrasonic matrix phased array 402 can produce sound waves in the direction 411 of travel of the longitudinal test object 10, against the direction 412 of travel of the longitudinal test object 10, perpendicular 413 to the surface of the longitudinal test object 10, in a radial clockwise direction 414, in a radial counterclockwise direction 415, in a first oblique direction 416, and in a second oblique direction 417.

Figure 7:
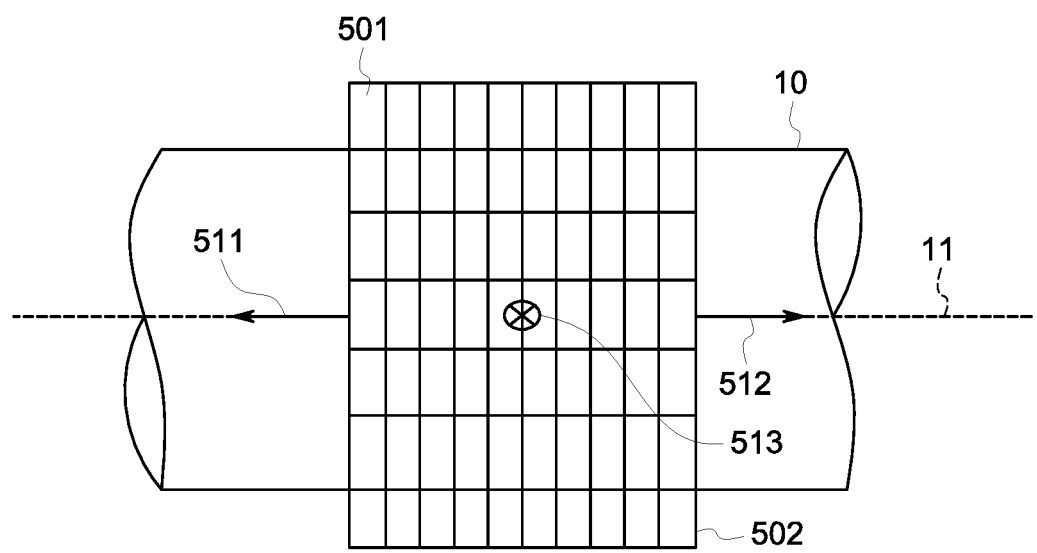
FIG. 7 is another illustrative diagram of an embodiment of a two-dimensional (1.5D) curved ultrasonic matrix phased array inspecting a longitudinal test object.

FIG. 7 is another illustrative diagram of an embodiment of a curved ultrasonic matrix phased array 502 inspecting a longitudinal test object 10 having a longitudinal axis 11. For illustrative purposes, FIG. 7 only shows the curved ultrasonic matrix phased array 502 for one of the plurality of curved ultrasonic matrix phased array probes 310 (FIG. 3)

that would surround the test chamber 320 (FIG. 3). The embodiment of a curved ultrasonic matrix phased array 502 includes a plurality of transducers 501 arranged in a two-dimensional array (1.5D) with an asymmetrical density vertically and horizontally. As discussed above, by activating certain groups of transducers 501, the curved ultrasonic matrix phased array 502 can transmit ultrasonic sound waves at various angles to identify flaws of any orientation. For example, the curved ultrasonic matrix phased array 502 can produce sounds waves in the direction 511 of travel of the longitudinal test object 10, against the direction 412 of travel of the longitudinal test object 10, and/or perpendicular 413 to the surface of the longitudinal test object 10.

The use of a plurality of curved ultrasonic matrix phased array probes 310 along with the rotating water jacket 382 can enable the identification of all surface and sub-surface flaws in a longitudinal test object, including core flaws, longitudinal flaws, transverse flaws, oblique flaws, lamination flaws, as well as the determination of wall thickness, inside diameter, and outside diameter.

Figure 8:
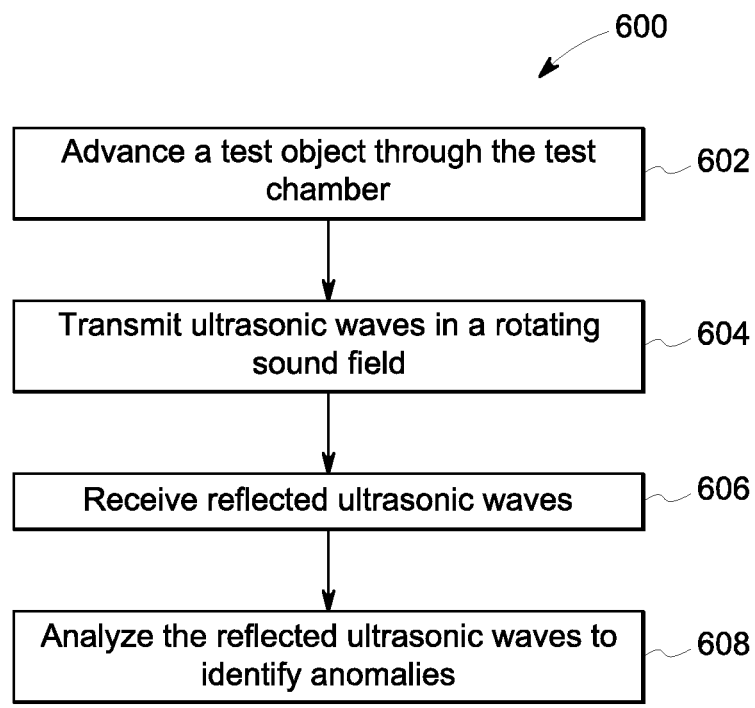
FIG. 8 is a flow diagram illustrating a method of inspecting a test object.

FIG. 8 is a flow diagram of a method of inspecting a test object 10. The method 600 can be employed by an inspection system, such as the inspection system 300 described above with regard to FIGS. 3-5B. At block 602, the test object 10 is advanced through the test chamber 320 defined by the plurality of phased array probes 310 and the plurality of fluid injectors 380 along the axis A. The fluid injectors 380 can generate or establish a rotating fluid jacket around the test object 10 as the test object 10 advances through the test chamber 320. At block 604, the plurality of phased array probes 310 transmit ultrasonic waves in a rotating sound field around a circumference of the test object 10 as the test object 10 advances through the test chamber 320. As discussed above, subsets 103, 104 (FIG. 1) of the ultrasonic transducers 101 (FIG. 1) of the phased array probes 310 can sequentially transmit ultrasonic waves to produce the rotating sound field. The ultrasonic waves are directed around the circumference of the test object 10. When the ultrasonic waves encounter an anomaly 110, 111 (FIG. 1) in the test object 10, such as a flaw or a defect, at least a portion of the ultrasonic waves are reflected from the anomaly 110, 111. At block 606, the reflected ultrasonic waves are received by the ultrasonic transducers 101 of the phased array probes 310. At block 608, the reflected ultrasonic waves are analyzed to identify, and in some examples characterize, the anomalies. In an example, a computing device (not shown) can be coupled to the phased array probes 310 to analyze the reflected ultrasonic waves.

In view of the foregoing, embodiments of the invention provide a method for inspecting longitudinal test objects. A technical effect is to enable inspection of longitudinal test objects and identification of flaws without requiring rotation of the test object or of the ultrasonic probes.

This written description uses examples to disclose the invention, including the best mode, and also to enable any person skilled in the art to practice the invention, including making and using any devices or systems and performing any incorporated methods. The patentable scope of the invention may include other examples that occur to those skilled in the art. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Other embodiments are within the scope and spirit of the disclosed subject matter.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

What is claimed is:

1. An ultrasonic inspection system comprising:
    a test chamber configured to receive a test object, the test chamber comprising:
        a plurality of ultrasonic probes aligned coaxially along an axis, each ultrasonic probe comprising a phased array of ultrasonic transducers, and
        a plurality of fluid injectors interspersed with the plurality of ultrasonic probes coaxially along the axis and configured to generate a rotating fluid jacket around the test object,
        wherein an interior surface of the plurality of ultrasonic probes and an interior surface of the plurality of fluid injectors define the test chamber; and
    a fluid supply system coupled to the plurality of fluid injectors to supply fluid to the plurality of fluid injectors,
    wherein the plurality of ultrasonic probes is configured to generate ultrasonic waves in a rotating sound field around a circumference of the test object to identify an anomaly in the test object.

2. The ultrasonic inspection system of claim 1, wherein the test object is a longitudinal test object.

3. The ultrasonic inspection system of claim 1, wherein the plurality of ultrasonic probes is configured to remain in a fixed position during inspection of the test object.

4. The ultrasonic inspection system of claim 1, wherein each ultrasonic probe of the plurality of ultrasonic probes and each fluid injector of the plurality of fluid injectors has a curved interior surface.

5. The ultrasonic inspection system of claim 4, wherein a curvature of the interior surface of each ultrasonic probe equals a curvature of the interior surface of each fluid injector.

6. The ultrasonic inspection system of claim 1, wherein each ultrasonic probe of the plurality of ultrasonic probe is located in a different plane and radially offset at a predetermined angle from an adjacent ultrasonic probe.

7. The ultrasonic inspection system of claim 6, wherein the predetermined angle is selected from the range of 0 degrees to 180 degrees.

8. The ultrasonic inspection system of claim 6, wherein the predetermined angle is selected from the range of 30 degrees to 120 degrees.

9. The ultrasonic inspection system of claim 1, wherein the test chamber defines a linear travel path along the axis for the test object.

10. The ultrasonic inspection system of claim 1, wherein the ultrasonic waves are configured to penetrate into the test object to identify anomalies within the test object.

11. An ultrasonic inspection system comprising:
    a plurality of ultrasonic probes, each ultrasonic probe comprising a phased array of ultrasonic transducers including a curved interior surface, the plurality of ultrasonic probes aligned along an axis to define a test chamber,
    wherein the plurality of ultrasonic probes is configured to transmit ultrasonic waves to a test object in the test chamber to identify anomalies in the test object with the plurality of ultrasonic probes configured to remain in a fixed position during inspection of the test object; and
    wherein each ultrasonic probe of the plurality of ultrasonic probe is located in a different plane and radially offset at a predetermined angle from an adjacent ultrasonic probe such that the interior surfaces of plurality of ultrasonic probes completely surround the test object in the test chamber.

12. The ultrasonic inspection system of claim 11, further comprising a plurality of fluid injectors interspersed among the plurality of ultrasonic probes and aligned coaxially with the plurality of ultrasonic probes along the axis.

13. The ultrasonic inspection system of claim 12, wherein each fluid injector of the plurality of fluid injectors comprises a at least one nozzle for discharging fluid, the plurality of fluid injectors configured to generate a rotating fluid jacket around the test object.

14. The ultrasonic inspection system of claim 13, wherein the plurality of fluid injectors is configured to discharge the fluid tangentially to an interior surface of each fluid injector and to the test chamber to produce the rotating fluid jacket.

15. The ultrasonic inspection system of claim 11, wherein the plurality of ultrasonic probes comprises four ultrasonic probes offset from each other by an angle of 90 degrees.

16. A method for inspecting a test object, the method comprising:

advancing a test object through a test chamber of an ultrasonic inspection system, the test chamber defined by a plurality of phased array ultrasonic probes and a plurality of fluid injectors, wherein the plurality of phased array ultrasonic probes is aligned along an axis and each probe has a curved interior surface and an array of ultrasonic transducers, wherein the plurality of fluid injectors are interspersed among the plurality of phased array probes along the axis and each fluid injector comprises a curved interior surface, and wherein the interior surfaces of the ultrasonic probes and the interior surfaces of the fluid injectors define the test chamber;

transmitting, via the ultrasonic transducers of the plurality of ultrasonic probes, ultrasonic waves in a rotating sound field around a circumference of the test object as the test object advances through the test chamber; and receiving, at the ultrasonic transducers, ultrasonic waves reflected from the test object.

17. The method of claim 16, further comprising generating, via the fluid injectors, a rotating fluid jacket around the test object as the test object advances through the test chamber.

18. The method of claim 16, further comprising identifying anomalies in the test object without rotating the test object and the plurality of ultrasonic probes.

19. The method of claim 16, further comprising analyzing the reflected waves to identify anomalies in the test object.

* * * * *